United States Patent [19]

Kino et al.

[11] Patent Number: 4,513,749
[45] Date of Patent: Apr. 30, 1985

[54] THREE-DIMENSIONAL TEMPERATURE PROBE

[75] Inventors: Gordon S. Kino, Stanford; Simon D. Bennett, Palo Alto; Didier Husson, Stanford, all of Calif.

[73] Assignee: Board of Trustees of Leland Stanford University, Stanford, Calif.

[21] Appl. No.: 442,567

[22] Filed: Nov. 18, 1982

[51] Int. Cl.³ .............................................. A61B 5/00
[52] U.S. Cl. ....................................... 128/660; 128/736; 374/119; 73/597
[58] Field of Search ................ 128/736, 660; 374/119, 374/117; 73/597, 598

[56] References Cited

U.S. PATENT DOCUMENTS

| 2,934,756 | 4/1960 | Kalmus | 374/119 |
|---|---|---|---|
| 3,320,808 | 5/1967 | Bold et al. | 374/119 |
| 3,604,252 | 9/1971 | Beeken | 374/119 |
| 3,771,355 | 11/1973 | Sachs | 128/660 |
| 4,201,087 | 5/1980 | Akita et al. | 374/119 |
| 4,215,575 | 8/1980 | Akita et al. | 374/119 |
| 4,215,582 | 8/1980 | Akita | 374/119 |
| 4,233,843 | 11/1980 | Thompson et al. | 374/119 |
| 4,416,552 | 11/1983 | Hessemer | 374/117 |
| 4,431,008 | 2/1984 | Wanner et al. | 128/660 |

FOREIGN PATENT DOCUMENTS

| 124028 | 9/1981 | Japan | 374/119 |
|---|---|---|---|
| 1227064 | 3/1971 | United Kingdom | 374/119 |

OTHER PUBLICATIONS

Sachs et al., Physics in Med. and Biol., vol. 22, No. 2, pp. 327-340, Mar. 1977.

*Primary Examiner*—Lee S. Cohen
*Assistant Examiner*—John C. Hanley
*Attorney, Agent, or Firm*—Burns, Doane, Swecker & Mathis

[57] ABSTRACT

Two coaxial acoustic beams, one focused and the other unfocused, are used to measure changes in temperature within a localized region in a body. The focal region of the focused beam is located at the area to be measured. Changes in the relative phase angle between the two beams are indicative of changes in acoustic properties occurring at the focal region. Since the two beams have generally the same propagation path outside of the focal region, they will be similarly affected by acoustic variations which occur there, so there will not be any relative phase change between them due to such variations.

22 Claims, 4 Drawing Figures

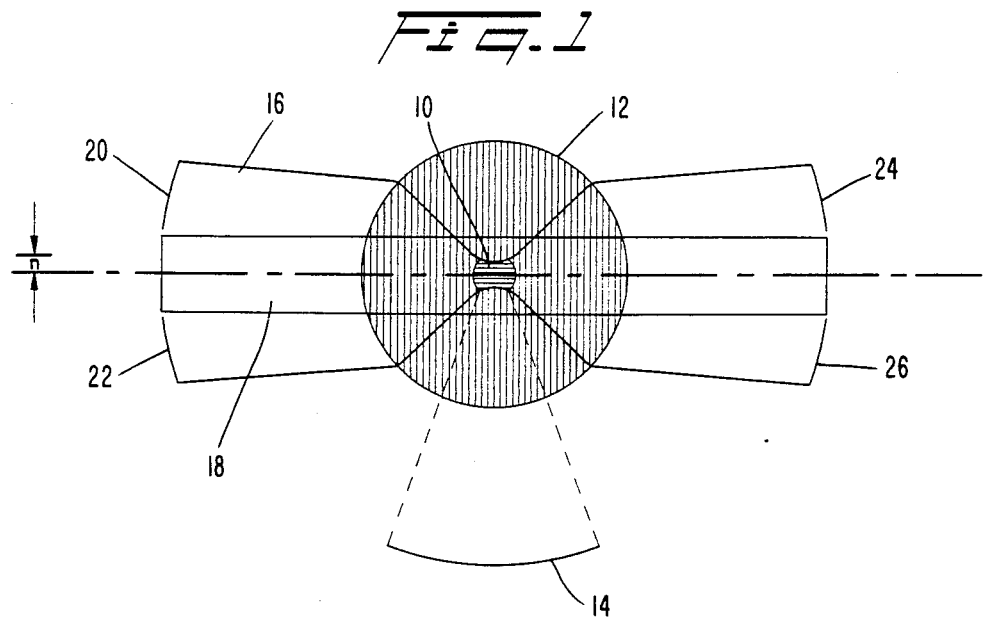
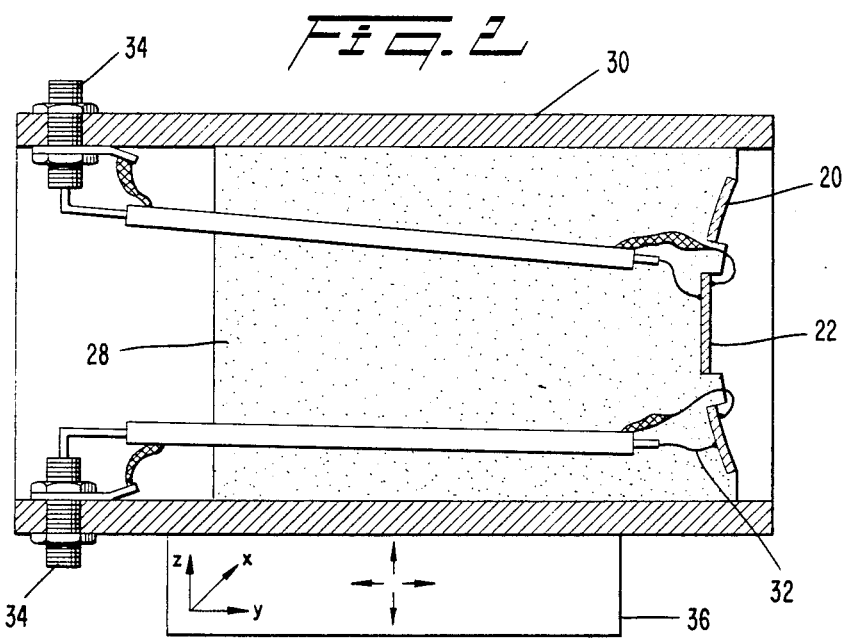

THREE-DIMENSIONAL TEMPERATURE PROBE

The invention described and claimed herein was made with Government support under Contract No. F49620-79-C-0217 awarded by the Air Force Office of Scientific Research. The U.S. Government has certain rights in the invention.

BACKGROUND OF THE INVENTION

The present invention is generally directed to the measurement of temperature, and more particularly to a novel method and apparatus for providing a three-dimensional indication of temperature variations within the interior of a body.

One field in which it is particularly desirable to be able to accurately measure temperature within the interior of a body is in the treatment of tumors by hyperthermia. Basically, this treatment approach involves the localized heating of the tumor to a specific temperature greater than normal body temperature. The localized heating is typically provided with a focused acoustic beam whose focal region is located in the tumor. During the treatment, it is necessary to monitor the temperature of the tumor tissue in order to be able to accurately control the frequency and/or intensity of the heating beam to assure that the tumor is being heated to the optimum temperature. Improper heating might result in either ineffectual treatment (not enough heat) or burning (too much heat).

In the past, the measurement of the temperature of the tumor tissue has been performed with invasive techniques, wherein a temperature sensitive device is inserted into the patient's body to be placed in direct physical contact with the tumor tissue. For example, the temperature sensing device could be a thermocouple attached to the end of a hypodermic needle. Other approaches might use fiber optics or similar such structures. The use of invasive temperature measuring techniques is undesirable in that the number of points at which temperature measurements can be made is limited due to the physical constraints on the number of invasive probes than can be practically utilized. In other words, only a sparse sampling of the temperature profile for the heated volume is available. In hyperthermia, as well as in other applications, it is important to be able to sample hundreds of individual points and obtain very fine resolution of the temperature profile, on the order of a few millimeters or less, for example. Other drawbacks associated with invasive techniques are that they require at least a minor incision and result in discomfort for the patient. In addition, they are limited in practical applications to the measurement of temperature in tumors located relatively close to the skin surface. They are not well suited for use in connection with deep-seated tumors or tumors that are located on or adjacent to sensitive vital organs.

Accordingly, it is a general object of the present invention to provide a novel method and apparatus for internally measuring the temperature of a body that does not require the use of invasive techniques. In this regard, it is an object of the invention to measure changes in the acoustic propagation properties of a body, to thereby provide an indication of temperature variations within the body.

The use of an acoustic signal to detect inhomogeneities or determine other internal properties of a body is generally known. For example, two similar acoustic inspection systems are disclosed in U.S. Pat. Nos. 3,233,450 and 3,771,355 issued to William J. Fry and Thomas D. Sachs, respectively. In the systems of these patents, a focused acoustic beam is used to excite, e.g. heat, the body to be measured in the area of interest. The excitation produces a temporary change in the acoustical characteristics in the region of the focal plane of the beam. A second acoustic beam, i.e. a sensing beam, is directed through the excited region of the body. The changes in acoustical characteristics, e.g. propagation velocity, are detected by the sensing beam. In the system of the Fry patent, the sensing beam detects the changes as the body is being excited. In the Sachs system, the acoustical characteristics are determined in the absence of any excitation and then again after the excitation has been applied.

Although the measurement of changes in acoustic properties has proven to be a viable noninvasive technique for determining internal characteristics of a body, heretofore known systems for practicing this technique are not without limitations. Foremost among these is the fact that the acoustic characteristic being detected, i.e. the velocity of the acoustic waves in the sensing beam, is averaged along the propagation path of the beam. The known systems do not have the capability to distinguish between changes occurring within the region of interest and changes outside of this region but within the sensing beam path. For example, where it is desired to monitor the heating of a tumor located within the liver of a person, the propagation velocity of the acoustic wave is going to be affected not only by the change in temperature of the tumor but also by movement of the liver caused by the action of the patient's breathing and the resulting motion of the diaphragm muscle, for example.

Due to this limitation, the prior systems are not well suited to scanning, for example to obtain a gradient profile of a particular area within the interior of a body. In other words, as the location of the beam is varied during scanning, its propagation path is going to change and thus any differences within the body but outside the area of interest will affect the detected result. Referring to the previous example, as the sensing beam is moved along the patient's abdomen to obtain a temperature profile of the liver tumor, the varying thickness of bones, muscle and other tissue that the beam must pass through will result in changes in the average velocity of the acoustic waves.

It is therefore another object of the present invention to provide a novel acoustic detection system for determining an internal characteristic of a body that is insensitive to variations occuring outside the region of interest.

It is a further object of the present invention to provide a novel acoustic detection system that examines acoustic characteristics of a body in a localized area and that can be scanned in three dimensions without being seriously degraded by variations outside the localized area.

SUMMARY OF THE INVENTION

Broadly speaking, these objects are achieved in accordance with the present invention by utilizing two coaxial acoustic beams to detect changes in the acoustic properties of a region within a body. One of the beams is a focused beam having its focal plane located in the region of interest, to provide spatial definition of the area whose property is being measured. The other beam is an unfocused one that has generally the same propagation path as the focused beam, except at its focal plane. Since the two beams encounter approximately the same conditions in most of the propagation path, both will be similarly affected by changes in acoustic properties that occur in their common path. However, in the focal region of the focused beam, the cross-sectional area of the two beams are different and they can detect differences in acoustic properties. Variations in the phase angle between the two beams are measured to indicate the detected differences. Hence, the unfocused beam essentially functions as a reference to negate the effects of acoustic properties outside the focal region of the focused beam.

As an alternative to using an unfocused beam as the reference, it is also possible to use a focused beam of a different frequency to provide the reference. The two focused beams will have different propagation paths, i.e. different cross-sectional areas, in their focal regions, and this will function in a manner similar to the embodiment using the unfocused beam.

Further features of the invention and the advantages provided thereby are explained in detail hereinafter with reference to particular embodiments of the invention illustrated in the accompanying drawings.

BRIEF DESCRIPTION OF THE DRAWINGS

FIG. 1 is a schematic wave propagation diagram illustrating the basic operating principles of the present invention;

FIG. 2 is a cross-sectional side view of a transducer assembly that can be used in the practice of the invention;

DETAILED DESCRIPTION

Figure 3:
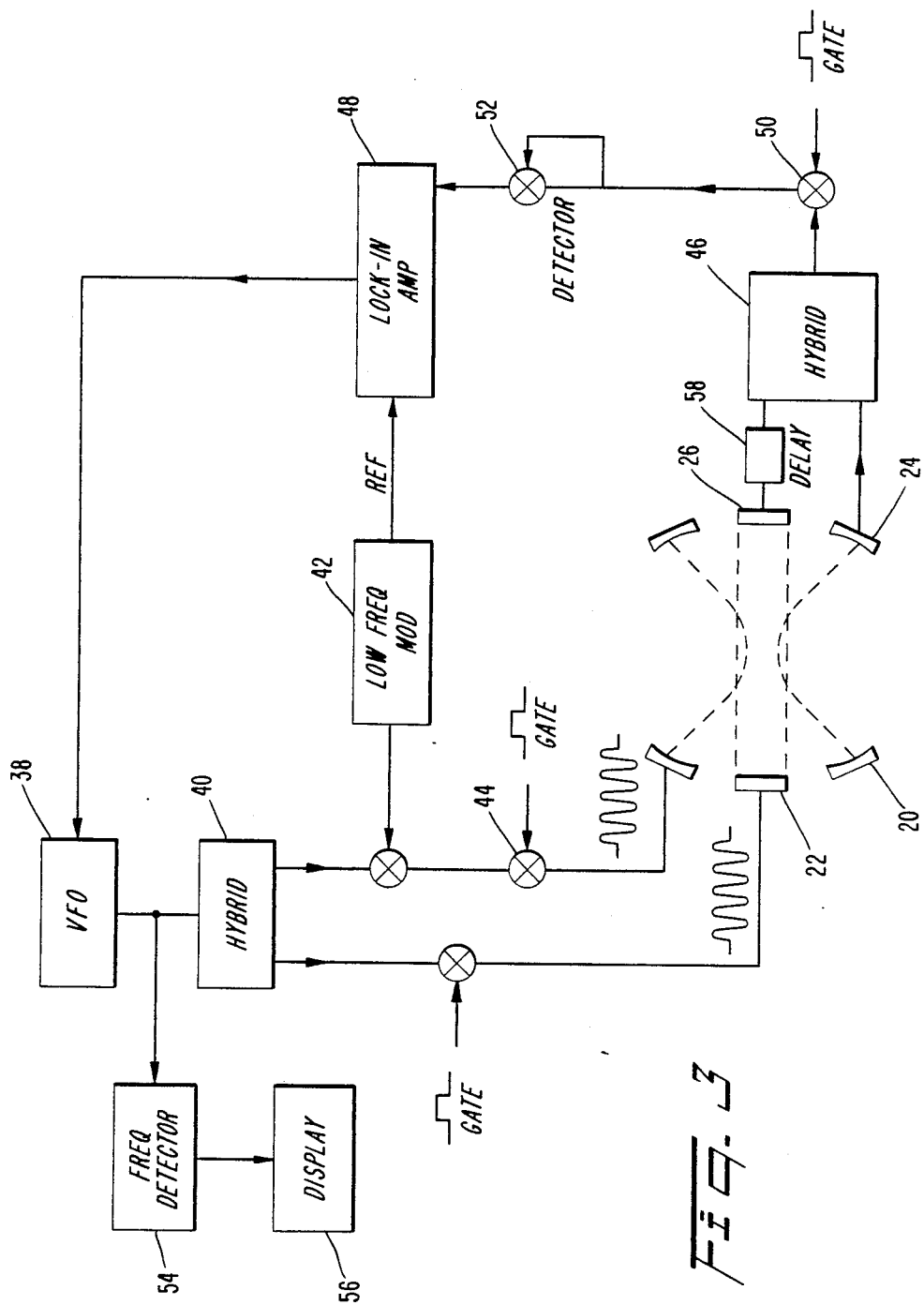
FIG. 3 is a schematic circuit diagram of a circuit for measuring the change in phase-difference between received signals.

In the following description of preferred embodiments of the invention, reference is made thereto in the context of acoustically monitoring the temperature of a tumor during the hyperthermic treatment thereof, to facilitate an understanding of the invention. It will be appreciated by those having familiarity with acoustic detection, however, that the invention is not so limited, but rather can find useful application in a variety of situations in which it is desirable to measure variations in temperature in a region within the interior of a body. For example it can be used to determine temperature within a flame, measure temperature of hot or molten steel such as in a casting environment, or determine ocean temperature fluctuations.

In fact, the invention is not limited to temperature measurement, and can be used to measure variation of practically any characteristic of a body that affects acoustic transmission through the body. Similarly, it is applicable to electromagnetic energy outside of the acoustic wavelength range, and can be used with optical or microwave beams, for example. The only constraints in this regard are that the beam be capable of being focused and that it be measurably affected by the body characteristic being detected.

The basic operating principle of the invention is best explained with reference to FIG. 1. In the example illustrated therein, the temperature of a tumor 10 within the neck or chest of a human body 12 (represented in a cross-sectional top view) is to be monitored. The monitoring may be performed while the tumor is being hyperthermically treated by means of a focused acoustic beam from a transducer 14, for example.

Changes in the temperature of the tumor will affect the velocity at which an acoustic wave passes through it. In accordance with one embodiment of the invention, two coaxial acoustic beams 16 and 18 having the same frequency are passed through the body 12 and the tumor 10. One of the beams, 16, is a focused beam having its focal region centered on the tumor. This beam can be produced by a transducer 20 having an appropriate concave, e.g. spherical, surface. The other beam, 18, is unfocused and can be produced by a flat transducer 22 located within an aperature in the transducer 20. After passing through the body, the two beams are received by two transducers 24 and 26 similar to the transducers 20 and 22, respectively.

The two beams 16 and 18 are configured so that the diameter $d_f$ of the focused beam at its focal region is much less than that, $d_u$, of the un-focused beam ($d_f < < d_u$). However, ever, outside of the focal region the two beams have generally the same propagation path within the body. Consequently, changes that affect the acoustic velocity and that are outside of the focal region will have the same effect on both beams, so that there will not be any relative change between them. On the other hand, a change in temperature of the tumor 10 will have a significant effect on the velocity of the focused beam 16 but little effect on the unfocused beam 18, assuming the cross-sectional area of the beam 18 is substantially greater than the area being heated by the beam from the transducer 14. Thus, the two beams will experience a relative phase change. Measurement of this phase change provides an accurate indication of the variation in temperature of the tumor, and can be used to control the frequency or intensity of the heating beam from the transducer 14 to regulate the temperature.

Thus, the focal region of the focused beam 16 functions to spatially define, or localize, the area being measured, and the unfocused beam 18 acts as a reference to cancel or diminish the effects of acoustic changes in areas outside the focal region.

This basis of operation also enables the two beams to be scanned in any direction to probe the tumor and obtain a temperature gradient profile. For example, if the beams are moved together in a direction perpendicular to their common axis a distance $x > d_f$, the change in phase angle of both beams in the region outside the focal region will be essentially the same. Near the focal region, however, a small movement $d_u > x > D_f$ will not affect the phase of the unfocused beam 18. A change in temperature over this region would shift the phase of the focused beam. The shift in the relative phase angle of the two beams provides an indication of the temperature variation. Thus the beams can be scanned together to measure the change in temperature over distance. This operation holds true for movement of the beams along their common axis as well as in a direction perpendicular thereto.

One type of transducer arrangement for generating or receiving the acoustic measuring signals 16 and 18 is illustrated in greater detail in FIG. 2. Each of the two coaxial transducers 20 and 22 can be a sheet of suitable poled ceramic or other piezoelectric material, such as PZT-5A for example. The central transducer 22 is a flat disc of the material, to produce an essentially parallel beam. The annular transducer 20 has a radius of curvature that is determined according to the depth of field that is desired, i.e. the distance from the transducer to the focal region. Alternatively, a suitable lens could be used to focus the beam. The angle of the beam produced by the transducer 20 should also take into account any interfacing mediums through which the beam is expected to propagate. In other words, as the beam passes from a surrounding medium, e.g. water, into the body, its convergence angle will change due to the different acoustic transmission properties of the two media. This change must be accounted for in determining the focal length of the beam.

The two sheets of transducer material are mounted on a bed 28 of suitable potting material within a housing 30. The potting material can be an epoxy impregnated with silicon carbide, for example, which has been found to enlarge the bandwidth of signals that can be generated by the transducers. Electrical leads 32 embedded within the potting material connect the transducers 20 and 22 to connector terminals 34 on the housing. The entire structure can be mounted on an X-Y-Z table 36, or the like, to enable the transducers to be scanned in any of three orthogonal directions.

One example of a circuit for controlling the transducers and measuring the relative phase change of the received acoustic signals is illustrated in FIG. 3. The output signal of a variable frequency oscillator 38 is applied to a hybrid circuit 40 that divides it into two signals of equal amplitude and frequency. One of these two signals is modulated with a low frequency signal from a modulator 42. The output signal from the oscillator 38 might be centered around 4 MHz and the modulation signal might be 1 KHz, for example. The modulated and unmodulated signals are respectively applied to the transducers 20 and 22 as tone bursts by suitable gate circuits 44.

The signals received by the transducers 24 and 26 are fed to a hybrid circuit 46 where they are combined to form a resultant signal. This resultant signal is applied to a lock-in amplifier 48 through a gate circuit 50 (synchronized with the gate circuits 44) and a square-law detector 52.

The output signal from the lock-in amplifier 48 is a signal at the modulation frequency (e.g. 1 KHz) whose amplitude is proportional to the cosine of the phase angle, i.e. the phase difference between the modulated and unmodulated carrier signals. This output signal is applied as the control input to the variable frequency oscillator 38.

In operation, the phase angle $\phi$ between the two received signals is defined as:

$$\phi = \omega(T_u - T_f) \quad (1)$$

where $\omega$ is the frequency of the acoustic signals, and $T_u$ and $T_f$ are the propagation times of the unfocused and focused signals, respectively. Thus, the change in the relative phase angle between the two signals, when frequency or transit time is altered, is defined as:

$$\delta\phi = \delta\omega(T_u - T_f) + \omega(\delta T_u - \delta T_f) \quad (2)$$

By controlling the output frequency of the variable frequency oscillator 38 with the output signal from the lock-in amplifier 48 in a negative feedback fashion, the phase angle of the two signals can be kept constant, i.e. $\delta\phi = 0$. For example the phase angle can be kept at 90° to make the output of the lock-in amplifier zero. In this case:

$$\delta\omega = \frac{\omega(\delta T_u - \delta T_f)}{T_u - T_f} \quad (3)$$

It will be appreciated that when the propagation times for the two signals are approximately the same, i.e. $T_u \simeq T_f$, the denominator in the right hand side of equation 3 is small and a large frequency shift, $\delta\phi$, is required to keep the phase shift constant for small changes in propagation time. In other words, accurate detection of small changes in the relative phase change between the two received signals is possible due to the large effective signal-to-noise ratio that is obtained.

These changes can be measured by a frequency detector 54 and indicated on a display unit 56. The display unit might be calibrated in terms of temperature, to provide a direct indication of the measured parameter. Alternatively, the input control voltage to the oscillator 38 from the lock-in amplifier 48 can be measured to provide an indication of variations in the relative phase angle.

If the range of frequencies required to detect changes in phase shift is larger than the operation bandwidth of the transducers, this range can be shortened by inserting an analog delay circuit 58 in the output line of one of the receiving transducers 24 or 26. The effect of this delay is to increase the denominator in the right-hand side of equation 3. Thus, smaller changes in frequency are required for each unit change in the relative phase difference between the two acoustic signals.

From the foregoing it will be appreciated that the present invention provides an acoustic detection system that can detect changes in acoustic properties in a localized region within the interior of a body without being affected by changes occurring outside the localized region. Experimental results have indicated that the localized region can be as small as a few millimeters in a direction transverse to the axis of the beams and about 1 centimeter along the axis. Temperature variations as small as 0.1°–0.2° C. can be detected in human tissue.

In the preceding illustration, the invention is explained with reference to the use of two transducers to generate two different acoustic beams of the same frequency. It is also possible to implement the invention with a single transducer that generates two focused beams having different frequencies, similar to that proposed for use in differential phase contrast imaging in scanning microscopes by I. R. Smith and H. K. Wickramasinghe in a paper entitled *Dichromatic Differential Phase Contrast Microscopy*. In this case, the widths of the focal regions of the two beams are respectively proportional to their frequencies. Thus, the lower frequency focused beam can be used as the reference beam and the higher frequency beam is used to define the region being measured.

Figure 4:
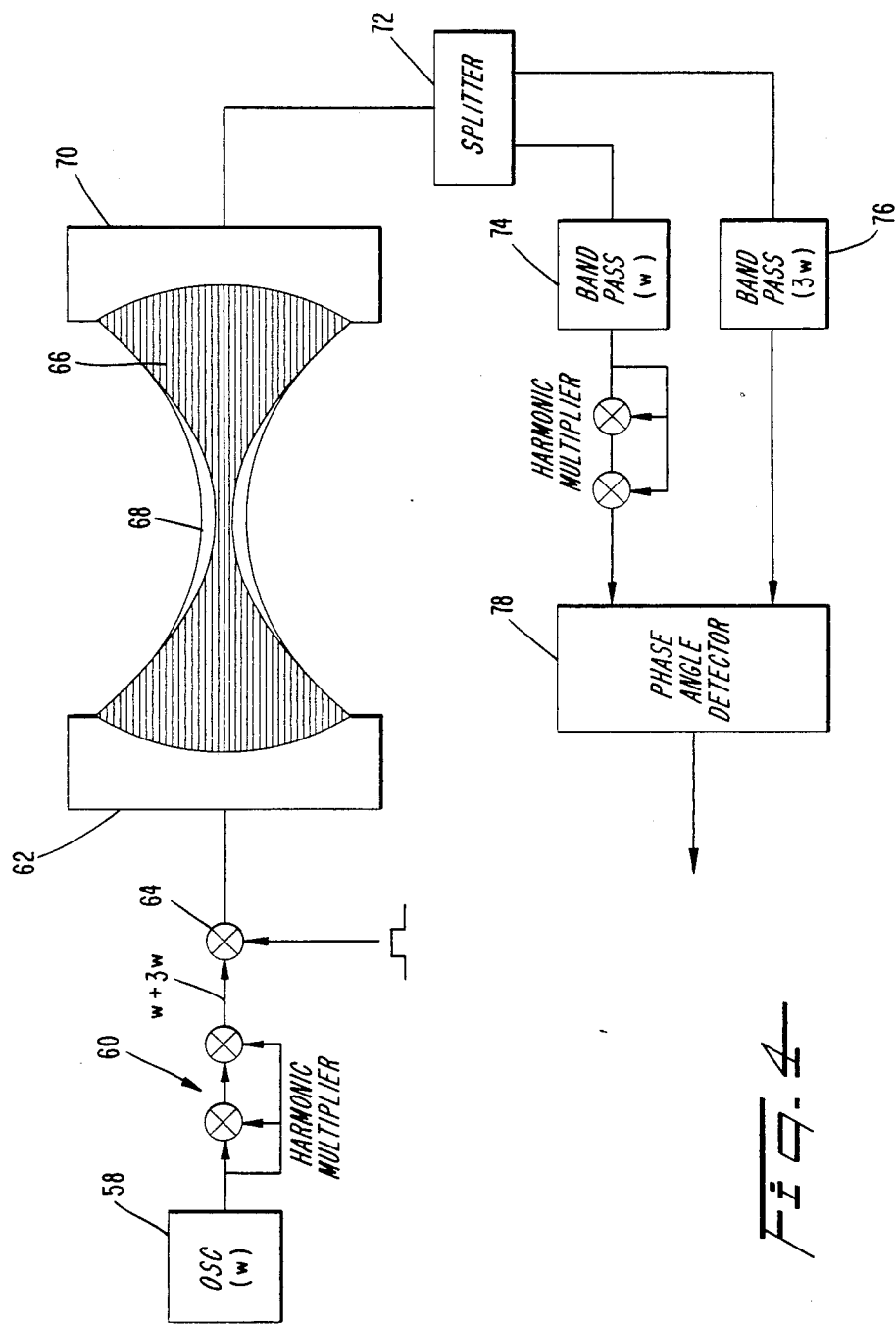
FIG. 4 is a schematic diagram of a second embodiment of the invention utilizing two focused beams.

A circuit for carrying out this embodiment is illustrated in FIG. 4. The output signal of an oscillator 58 is presented to an harmonic multiplier 60 to generate an excitation signal consisting of a fundamental frequency (1) and a suitable harmonic of that frequency (which is 31 in the illustrated embodiment). This excitation signal is applied to a transmitting transducer 62 through a gate circuit 64. The high frequency component (31) of the excitation signal causes the transducer 62 to generate a focused acoustic beam 66 having a relatively narrow focal region. This beam is shaded in FIG. 4. The acoustic beam 68 produced as a result of the low frequency component is substantially the same as the beam 66, except in the focal region, where its width is proportionately greater. It will be appreciated that the relative widths of the two beams in the focal region can be suitably adjusted by appropriate control of the excitation frequencies.

After propagation through the body being measured (not shown in FIG. 4), the beams 66 and 68 are received by a second transducer 70. A signal splitter 72 divides the output signal of the transducer 70 and presents the two resulting signals to two band pass filters 74 and 76. The lower frequency signal from the filter is harmonically multiplied for detection purposes, and the two signals are compared in a phase angle detector 78. This detector can be of the type depicted in greater detail in FIG. 3, for example. The detected phase angle can be used to indicate temperature changes, and control the output of the oscillator 58, as described previously.

Variations to the embodiments of the invention specifically disclosed herein are possible without compromising the advantages obtained thereby. For example, instead of using separate transmitting and receiving transducers located on opposite sides of the body, it is possible to use a single transducer to both transmit a signal and measure acoustic waves that reflect off an object. For example a bone, or an interface of two layers of tissue or structure within the body beyond the region being measured, can be used as the reflecting surface in a human body. This approach may be most desirable where the region to be measured is located close to one surface of the body and the acoustic waves are likely to be severely attenuated if they pass through the entirety of the body, or when the region being measured is inaccessible from one side of the body.

Another possible variation is the use of electronically focused acoustic beams rather than appropriately curved transducers. Thus it will be appreciated by those having an ordinary level of skill in the art that the presently disclosed embodiments are illustrative and not restrictive. The scope of the invention is indicated by the appended claims rather than the foregoing description, and all changes that come within the meaning and range of equivalents thereof are intended to be embraced therein.

What is claimed is:

1. Apparatus for internally measuring variations in a body that affect the transmission of an energy wave through the body, comprising:
   means for generating two coaxial energy beams, at least one of said beams being convergent and the other of said beams having generally the same cross-sectional area as said focused beam along most of the propagation path of said convergent beam and having a cross-sectional area that is greater than that of the convergent beam in the region of its convergence;
   means for receiving said two beams after propagation through the region of the body being measured;
   means for measuring changes in the relative phase angle between the received beams as an indication of variations in the body.

2. The apparatus of claim 1 wherein said energy beams are acoustic beams.

3. The apparatus of claim 1 wherein said two beams have the same frequency.

4. Apparatus for internally measuring variations of a parameter affecting acoustic properties within an object, comprising:
   means for transmitting a focussed acoustic beam being that converges upon a focal region;
   means for transmitting a second acoustic beam coaxially with said focussed beam, the cross-sectional area of said second acoustic beam being generally the same as the focussed beam outside of said focal region and greater than that of the focussed beam within said focal region;
   means for receiving said beams;
   means for measuring changes in the difference in velocities of the received beams; and
   means for displaying said changes as an indication of changes in the parameter.

5. The apparatus of claim 4 wherein said measuring means includes:
   means for detecting changes in the phase angle between the received beams;
   means responsive to said detecting means for controlling the output frequency of one of said transmitting means to maintain a predetermined phase angle between the received beams; and
   means for measuring the output frequency of said frequency controlled transmitting means, wherein changes in the output frequency reflect changes in the difference in velocities.

6. Apparatus for internally measuring temperature variations of a region within an object, comprising:
   means for transmitting a focussed acoustic beam that converges upon a focal region;
   means for transmitting a second acoustic beam coaxially with said focussed beam, the cross-sectional area of said second acoustic beam being generally the same as the focussed beam outside of said focal region and greater than that of the focussed beam within said focal region;
   means for receiving said beams;
   means for measuring changes in the difference in velocities of the received beams; and
   means for displaying the measured changes as an indication of temperature variations.

7. The apparatus of claim 6 wherein said measuring means includes:
   means for detecting changes in the phase angle between the received beams;
   means responsive to said detecting means for controlling the output frequency of one of said transmitting means to maintain a predetermined phase angle between the received beam; and
   means for measuring the output frequency of said frequency controlled transmitting means, wherein changes in the output frequency reflect changes in the difference in velocities.

8. A method for measuring variations of a parameter affecting the transmission of an energy wave through the interior of an object, comprising the steps of:
   transmitting a convergent energy beam into the object, said beam converging on a region in the area of the object wherein said parameter is to be measured;
   transmitting a reference energy beam into the object that is coaxial with said convergent beam, the cross-sectional area of said reference energy is generally the same as that of the convergent beam outside of said region and is greater than that of the convergent beam in said region;

receiving the convergent and reference energy beams after propagation through the region where said parameter is to be measured;

determining the relative phase angle between the two received beams; and measuring changes in the determined phase angle as an indication of changes in the parameter.

9. The method of claim 8 further including the step of scanning said beams to obtain a gradient profile of the parameter in the object.

10. The method of claim 9 wherein said beams are scanned in directions that are both parallel to and tranverse to the axis of propagation of said beams.

11. The method of claim 8 wherein said reference energy beam has the same frequency as said convergent beam.

12. The method of claim 8 wherein said convergent and reference energy beams are transmitted simultaneously.

13. The method of claim 8 wherein said reference beam is a convergent beam.

14. A method for measuring variations of a parameter affecting acoustic properties within the interior of an object, comprising the steps of:

transmitting a first acoustic beam into the object, said beam being focussed onto an area of the object wherein said parameter is to be measured;

transmitting a second acoustic beam into the object that is coaxial with said first beam, the cross-sectional area of said second beam being generally the same as that of the first beam outside of said area and being greater than that of said first beam within said area;

receiving the beams after propagation through the area where said parameter is to be measured;

determining the relative phase angle between the two received beams; and measuring changes in the determined phase angle as an indication of changes in the parameter.

15. The method of claim 14 further including the step of scanning said acoustic beams to obtain a gradient profile of the parameter in the object.

16. The method of claim 15 wherein said beams are scanned in directions that are both parallel to and transverse to the axis of propagation of said beams.

17. The method of claim 14 wherein the step of measuring changes in the determined phase angle includes the steps of adjusting the frequency of said acoustic beams to provide a predetermined phase angle between the two received beams, and measuring the changes in frequency that are required to maintain said predetermined angle.

18. A method for internally measuring variations in temperature of a region within an object, comprising the steps of:

transmitting a first acoustic beam into the object, said beam being focussed onto the region of the object wherein temperature variations are to be measured;

transmitting a second acoustic beam through said region of object, the cross-sectional area of said second beam in the object being generally the same as that of the first beam outside of the region and being greater than that of the first beam in said region;

receiving the first and second beams after propagation through the region of the object to be measured;

determining the relative phase angle between the two received beams;

measuring changes in the determined phase angle; and correlating the measured changes to variations in temperature.

19. The method of 18 wherein said second beam is coaxial with said first beam.

20. The method of claim 18 further including the step of scanning said acoustic beams to obtain a temperature gradient profile of the object.

21. The method of claim 20 wherein said beams are scanned in directions that are both parallel to and transverse to the axis of propagation of said beams.

22. The method of claim 18 wherein the step of measuring changes in the determined phase angle includes the steps of adjusting the frequency of said acoustic beams to provide a predetermined phase angle between the two received beams, and measuring the changes in frequency that are required to maintain said predetermined angle.

* * * * *